(12) United States Patent
Morita et al.

(10) Patent No.: US 7,978,208 B2
(45) Date of Patent: Jul. 12, 2011

(54) SYSTEMS AND METHODS FOR MULTI-SOURCE VIDEO DISTRIBUTION AND COMPOSITE DISPLAY

(75) Inventors: Mark M. Morita, Arlington Heights, IL (US); Yongjian Bao, Vernon Hills, IL (US)

(73) Assignee: General Electric Company, Schenectady, NY (US)

( * ) Notice: Subject to any disclaimer, the term of this patent is extended or adjusted under 35 U.S.C. 154(b) by 1108 days.

(21) Appl. No.: 11/735,733

(22) Filed: Apr. 16, 2007

(65) Prior Publication Data

US 2008/0252784 A1   Oct. 16, 2008

(51) Int. Cl.
*G09G 5/00* (2006.01)
*G09G 5/02* (2006.01)
*H04N 7/18* (2006.01)
*H04N 5/222* (2006.01)
*H04N 7/00* (2006.01)
*G06F 3/00* (2006.01)

(52) U.S. Cl. ........ 345/629; 345/581; 345/619; 345/630; 348/143; 348/153; 348/333.02; 348/552; 715/700; 715/719

(58) Field of Classification Search .................. 345/418, 345/581, 619, 629–630; 382/131–132; 715/700, 715/719, 763–764; 348/143, 153, 159, 207.1, 348/211.14, 211.12, 239, 552, 333.02, 563–565, 348/584

See application file for complete search history.

(56) References Cited

U.S. PATENT DOCUMENTS

| | | | |
|---|---|---|---|
| 5,130,794 A * | 7/1992 | Ritchey | 348/39 |
| 6,167,296 A | 12/2000 | Shahidi | |
| 7,787,699 B2 | 8/2010 | Mahesh et al. | |
| 2005/0108091 A1 * | 5/2005 | Sotak et al. | 705/14 |
| 2007/0016028 A1 | 1/2007 | Donaldson et al. | |
| 2007/0041660 A1 | 2/2007 | Mahesh et al. | |
| 2009/0040385 A1 * | 2/2009 | Staker et al. | 348/584 |
| 2010/0066762 A1 * | 3/2010 | Yeh et al. | 345/629 |
| 2010/0158109 A1 * | 6/2010 | Dahlby et al. | 375/240.03 |

FOREIGN PATENT DOCUMENTS

| | | |
|---|---|---|
| CN | 1939235 A | 4/2007 |
| EP | 1755059 | 2/2007 |
| EP | 1755059 A1 | 2/2007 |
| WO | WO 94/24631 A | 10/1994 |
| WO | WO 00/56215 A1 | 9/2000 |
| WO | WO 02/41136 A2 | 5/2002 |

OTHER PUBLICATIONS http://www.karlstorz.com/cps/rde/xchg/SID-0A010A01-C7127BB5/karlstorz-en/hs.xsl/522.htm.

(Continued)

*Primary Examiner* — Wesner Sajous
(74) *Attorney, Agent, or Firm* — McAndrews, Held & Malloy, Ltd.; Michael A. Dellapenna (57) ABSTRACT

Certain embodiments of the present invention provide a video display processing system including a video source input component, a compositing component, and a composite video output component. The video source input component is adapted to receive video data from a plurality of video sources. The compositing component is adapted to generate a composite video image from the video data. The composite video image is based at least in part on a configuration. The configuration specifies an arrangement of the video data. The composite video output component adapted to output the composite video image.

45 Claims, 6 Drawing Sheets

OTHER PUBLICATIONS http://www.stryker.com/endoscopy/y_integrated_or/.
One Company, One Solution brochure downloaded at http://www.ic-live.com/cr.php?cID=1360&cdid=3190&campID=8&convID=1197&ic_url=http://www.stryker.com/endoscopy/media/ISuite.pdf.

Graves, et al. "An Integrated Remote Neurosurgical System," CVRMED-MRCAS, '97 First Joint Conference, Computer Vision, Virtual Reality and Robotics in Medicine and Medical Robotics and Computer-Assisted Surgery Proceedings Springer-Verlag Berlin, Germany, 1997, pp. 799-808, XP002494610 ISBN: 3-540-62734-0, section 4.2 Interface Design.

Stryker, Endoscopy "Integrated Operating Rooms," http://www.stryker.com/endoscopy/Products/integOpRoom/iorEndosuite.html, 2004.
Stryker, Communications "Video, Voice & Data Integration," http://www.stryker.com/communications/VVandDI/vvdiNetworkHub.html, 2004.
Stryker, Communications "Video, Voice & Data Integration," http://www.stryker.com/communications/VVandDI/VVand DiMain.html, 2004.
Stryker, Communications "Video, Voice & Data Integration," http://www.stryker.com/communications/VVandDI/vvdiSwitchPoint.html, 2004.
State Intellectual Property Office, PR China—Office Action dated Mar. 16, 2011. pp. 1-12.

* cited by examiner

SYSTEMS AND METHODS FOR MULTI-SOURCE VIDEO DISTRIBUTION AND COMPOSITE DISPLAY

BACKGROUND OF THE INVENTION

The present invention generally relates to video processing. More specifically, the present invention relates to systems and methods for multi-source video distribution and composite display.

In many situations it is desirable to be able to display video data from more than one source on a single display screen. For example, a given operating environment may have limited space and more than one display may not be practical. As another example, a single video source may not be able to effectively utilize a large screen.

One situation in which video data streams from multiple sources may be displayed is in a healthcare environment such as an operating room for surgery or an interventional radiology suite. Current operating rooms and interventional radiology suites have a number of video screens hanging on booms or articulating arms. Typically, each video display is tied to a single information system or imaging modality. For example a typical operating room might have a Picture Archiving and Communication System ("PACS") with 1-3 displays, an electronic medical records ("EMR") system with one display, an ultrasound display, an acquisition workstation display, a fluoroscopy display, and a navigation display.

Figure 1:
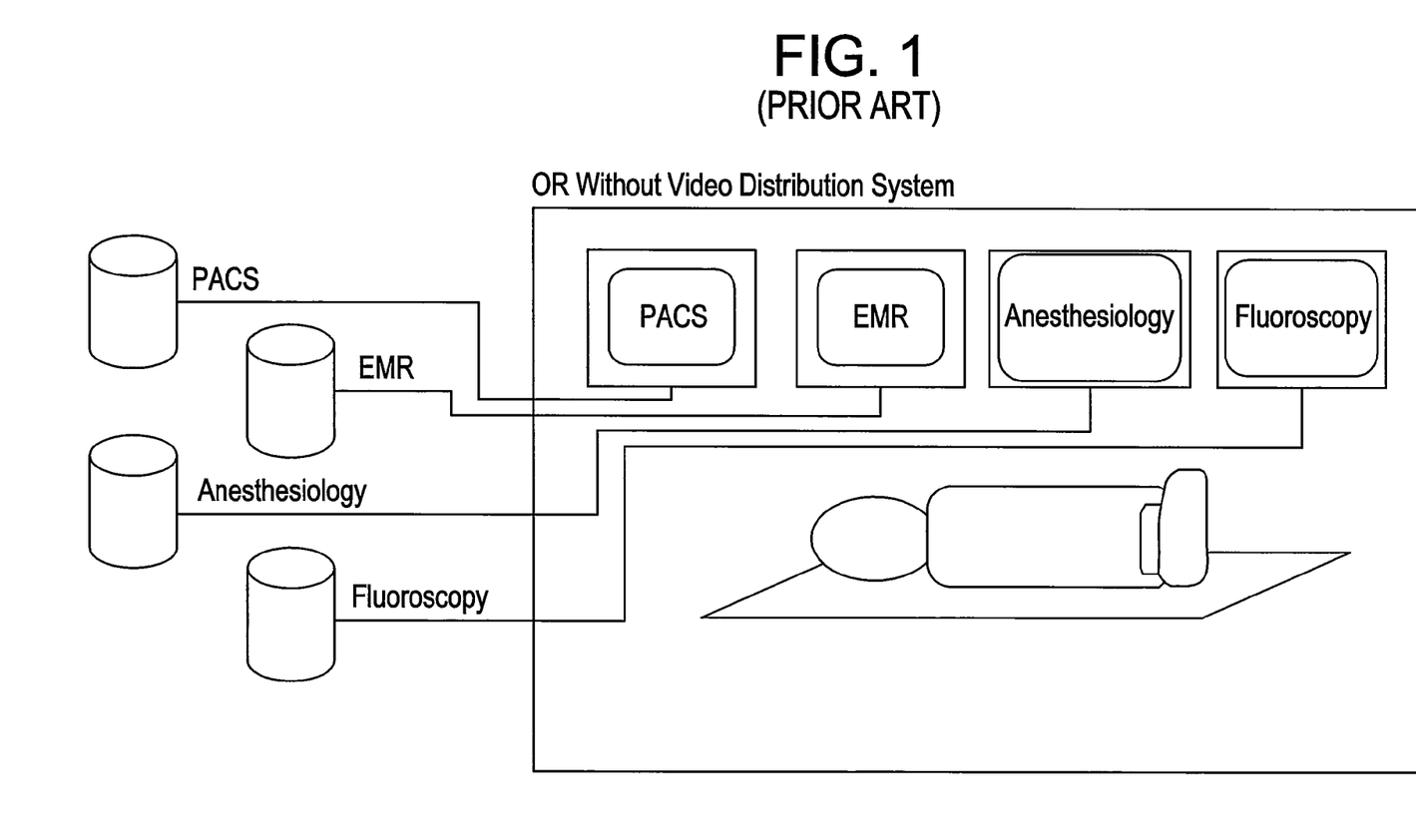
FIG. 1 illustrates an example of a current system for display of video data from multiple sources in an operating room.

FIG. 1 illustrates an example of a current system for display of video data from multiple sources in an operating room. As shown in FIG. 1, video data from various sources, such as a PACS, EMR, anesthesiology, and fluoroscopy systems, may each be displayed on a dedicated screen. That is, each system generates video data to be displayed on a separate display, specific to the video source. These displays not only contribute to information overload, but also make it extremely difficult to navigate to specific information needed to make life-critical decisions.

Figure 2:
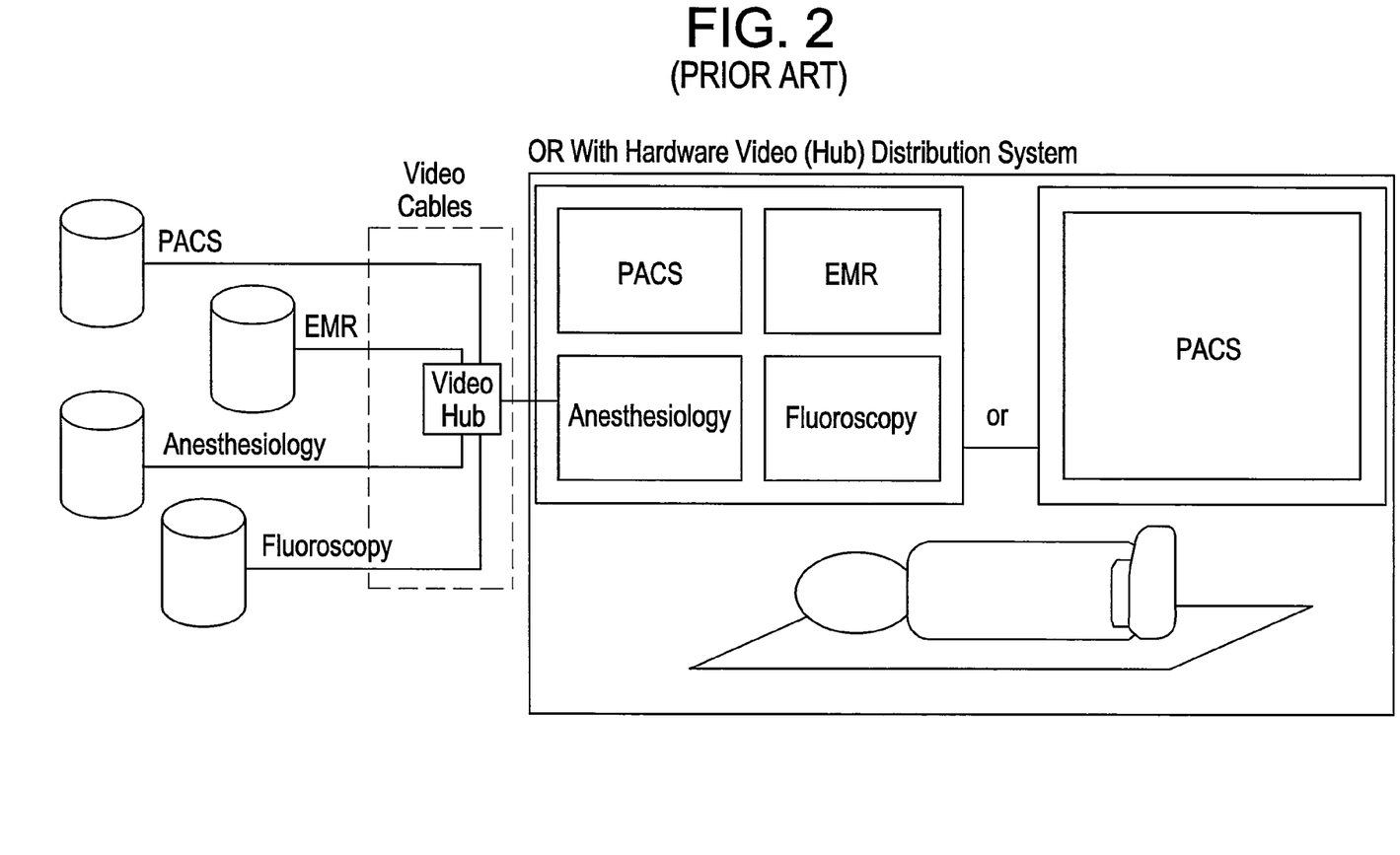
FIG. 2 illustrates an example of a current system for display of video data from multiple sources on a single screen in an operating room.

Video distribution systems have been used by hospitals to reduce some of the extraneous display clutter. FIG. 2 illustrates an example of a current system for display of video data from multiple sources on a single screen in an operating room. As shown in FIG. 2, video data is communicated from various video sources over video cables to a video hub. The video hub is typically a hardware video router. The video hub may then allow a user to select one of the different video sources for display. That is, only one video source is shown at a time, with the video hub controlling which source is currently selected. Alternatively, the video hub may partition the display into multiple viewports and scale the video data from each video source to occupy a section of the screen. A major problem with this method of video distribution is that each information source is still displayed in its own context, and only one video source can be "active" for user interaction. That is, other viewports may display dynamic information, but the ability to interact with disparate information systems simultaneously is not supported.

However, even with the use of a video hub, information overload still occurs. Users are forced into viewing information from disparate systems in multiple viewports, or sequentially switching them in the same viewport, all in their own context, without a true integration. The user is not able to display information from each system in a user-configurable, composite fashion, and interact with it. Additionally, video routing and/or combining hardware is expensive. Further, such systems have hard limits on the number of inputs. That is, many systems cannot manage more than a fixed number of video feeds.

Thus, there exists a need for systems and methods for multi-source video distribution and composite display.

BRIEF SUMMARY OF THE INVENTION

Certain embodiments of the present invention provide a video display processing system including a video source input component, a compositing component, and a composite video output component. The video source input component is adapted to receive video data from a plurality of video sources. The compositing component is adapted to generate a composite video image from the video data. The composite video image is based at least in part on a configuration. The configuration specifies an arrangement of the video data. The composite video output component adapted to output the composite video image.

Certain embodiments of the present invention provide a method for providing composite video including receiving video data from a plurality of video sources and generating a composite video image from the video data. The composite video image is based at least in part on a configuration. The configuration specifies an arrangement of the video data.

Certain embodiments of the present invention provide a computer-readable medium including a set of instructions for execution on a computer, the set of instructions including a video source input routine, a compositing routine, and a composite video output routine. The video source input routine is configured to receive video data from a plurality of video sources. The compositing routine is configured to generate a composite video image from the video data. The composite video image is based at least in part on a configuration. The composite video output routine is configured to output the composite video image.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 3:
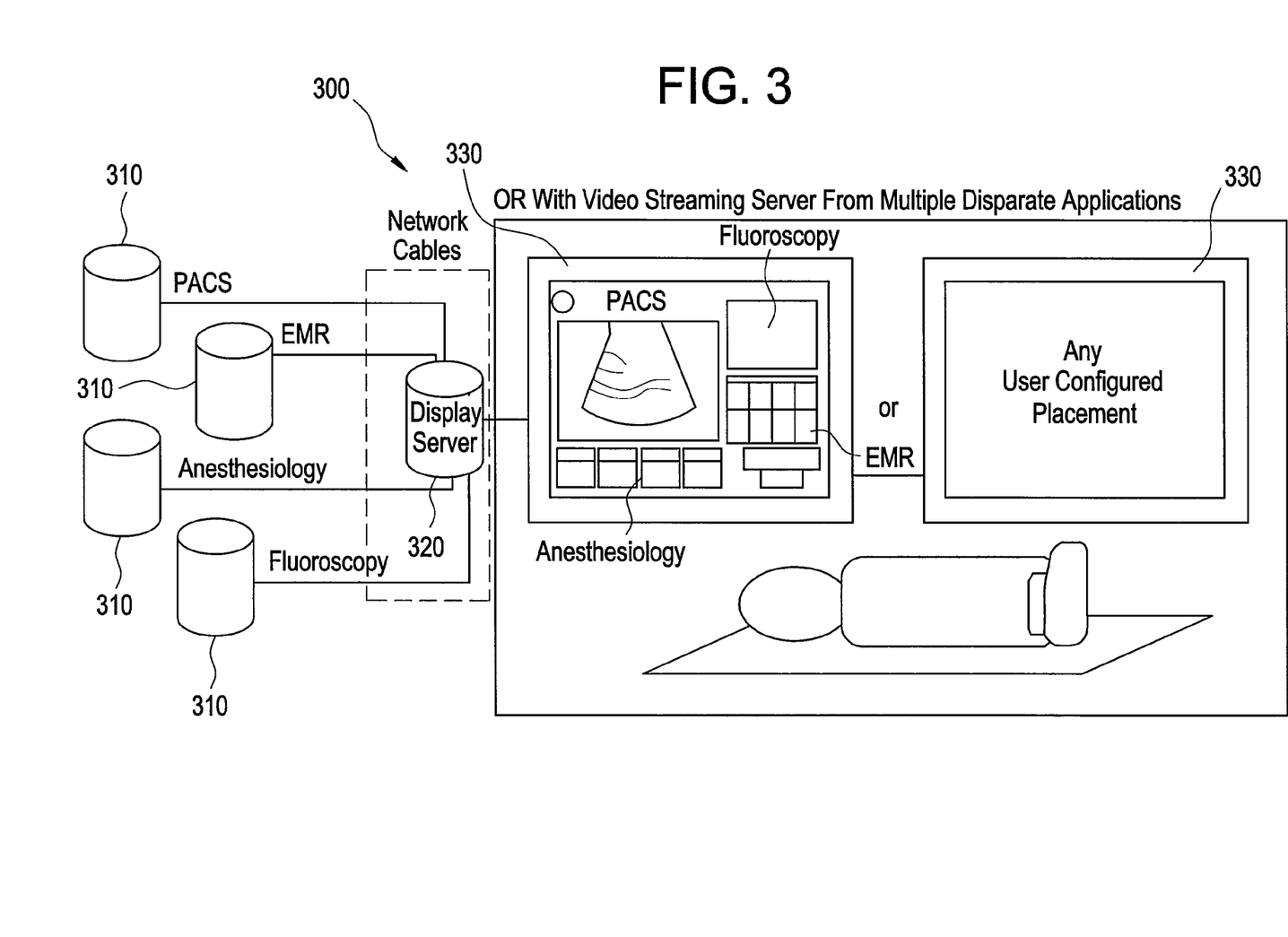
FIG. 3 illustrates a video content distribution system according to an embodiment of the present invention.

FIG. 3 illustrates a video content distribution system 300 according to an embodiment of the present invention. The system 300 includes one or more video data sources 310, a video display processing system 320, and a display 330.

The video display processing system 320 is in communication with the one or more video data source 310. The video display processing system 320 is in communication with the display 330.

In operation, video data is provided by the video data sources 310. The video data from each video data source 310 is communicated to the video display processing system 320. The video display processing system 320 combines the video data from each video data source 310 to generate a composite video image. The composite video image is then output from the video display processing system 320 to the display 330. The display 330 then displays the composite video image.

The video data may include information intended for display. For example, an application on a video data source 310 may generate video data that is intended to be displayed on a display such as the display 330.

As illustrated in the embodiment in FIG. 3, the video content distribution system 300 may be used in a healthcare facility, such as an operating room or an interventional radiology suite. The video data sources 310 may include, for example, a PACS, EMR, anesthesiology, and/or fluoroscopy systems, for example. For example, a video data source 310 may be a PACS workstation. As another example, a video data source 310 may be an imaging modality.

The video data sources 310 may communicate with the video display processing system 320 over a network, for example. For example, the video data sources 310 may communicate over a wired Ethernet network. As another example, the video data sources 310 may communicate over a wireless network. As another example, the video data sources 310 may communicate over coaxial video cables. The video data may be streaming video communicated to the video display processing system 320, for example.

The video display processing system 320 is adapted to receive video data from the video data sources 310. The video display processing system 320 is adapted to generate a composite video image from the received video data. That is, the video display processing system 320 is adapted to combine the received video data into a video image. For example, video data may be received by the video display processing system 320 from four video data sources 310. The video display processing system 320 may then combine the video data into a composite video image by allocating one quarter of the video image to the video data from each of the four video data sources 310. As another example, the video display processing system 320 may generate the composite video image by allocating differently shaped portions of the video image to the video data from each video data source 310, as illustrated in FIG. 3. As another example, the video display processing system 320 may combine fewer than all of the received video data into the composite video image. For example, while video data may be received from four video data sources 310, the composite video image may include video data from only two of the video data sources 310.

In certain embodiments, the video display processing system 320 generates the composite video image based at least in part on a configuration. The configuration specifies an arrangement of the video data. That is, the configuration describes how the video display processing system 320 should composite the received video data. For example, the configuration may indicate that video data received from one video data source 310 is to occupy half the screen, while video data from two other video data sources should split the remaining half of the screen one-third and two-thirds, respectively. The configuration may be user defined. That is, a user may specify a preferred arrangement of video data from various video data sources 310. For example, a surgeon might want to display only the following elements from specific systems: from a PACS, historical diagnostic radiography (DR) images; from an EMR system, patient allergies, current medications, and family history; from an anesthesiology system, patient vital signs; from a fluoroscopy system, live catheter positioning imagery; and from an ultrasound system, live positioning of needle or tumor.

In certain embodiments, the configuration is based at least in part on a medical procedure. For example, for a mammography biopsy procedure, the configuration may indicate that historical PET and ultrasound images be displayed along with live ultrasound and an EMR screen with demographic information and family history for the patient. As another example, for a cardiology procedure such as radio frequency ablation, the configuration may indicate that EKG information and other vital signs from an anesthesiology system be displayed along with live images from a fluoroscopy system and prior images from a PACS such as chest x-rays.

In certain embodiments, the configuration is based at least in part on a hanging protocol. That is, the configuration may be based on and/or include a Default Display Protocol (DDP) similar to that used by other components in a PACS. For example, different clinical scenarios may have different clinical baseline configurations that users may modify.

The display 330 may be a standard display device such as a television, computer monitor, LCD, or plasma screen, for example. The display 330 is adapted to display a video image output from the video display processing system 320. The display 330 may receive the output video image over a coaxial cable or a network, for example. For example, the output video may be provided using streaming video to the display 330.

In certain embodiments, the display 330 includes more than one screen. For example, the display 330 may include two or four screens that act as a single display.

The display 330 may display a composite video image in a manner similar to that illustrated in FIG. 5, discussed below, for example.

Figure 4:
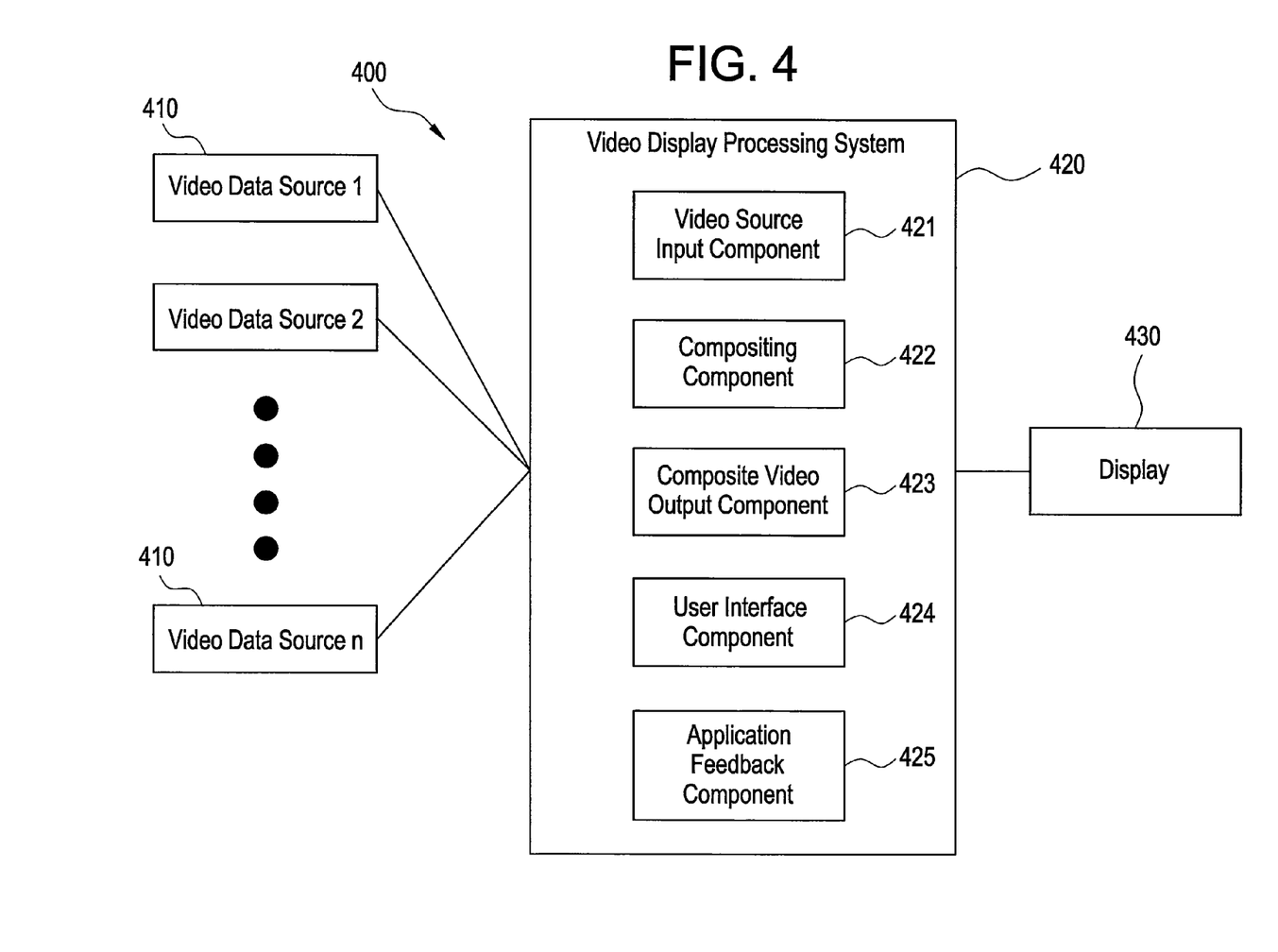
FIG. 4 illustrates a video content distribution system according to an embodiment of the present invention.

FIG. 4 illustrates a video content distribution system 400 according to an embodiment of the present invention. The system 400 includes one or more video data sources 410, a video display processing system 420, and a display 430.

The video display processing system 420 is in communication with the one or more video data sources 410. The video display processing system 420 is in communication with the display 330.

The one or more of the video data sources 410 may be similar to a video data source 310, described above, for example. The video display processing system 420 may be similar to the video display processing system 320, described above, for example. The display 430 may be similar to the display 330, described above, for example.

In operation, video data is provided by the video data sources 410. The video data from each video data source 410 is communicated to the video display processing system 420. The video display processing system 420 combines the video data from each video data source 410 to generate a composite video image. The composite video image is then output from the video display processing system 420 to the display 430.

The display 430 then displays the composite video image.

The video data may include information intended for display. For example, an application on a video data source 410 may generate video data that is intended to be displayed on a display such as the display 430.

The video content distribution system 400 may be used in a healthcare facility, such as an operating room or an interventional radiology suite. The video data sources 410 may include, for example, a PACS, EMR, anesthesiology, and/or fluoroscopy systems, for example. For example, a video data source 410 may be a PACS workstation. As another example, a video data source 410 may be an imaging modality.

The video data provided by a video data source 410 may be generated at least in part by an application. The application may run at least in part on the video data source 410. For example, an EMR software application may be running on a computer that is the video data source 410 and provides video data based on the EMR software application. As another example, the video data source 410 may include a software application such as an image view for an imaging modality.

The video data sources 410 may communicate with the video display processing system 420 over a network, for example. For example, the video data sources 410 may communicate over a wired Ethernet network. As another example, the video data sources 410 may communicate over a wireless network. As another example, the video data sources 410 may communicate over coaxial video cables. The video data may be streaming video communicated to the video display processing system 420, for example.

The video display processing system 420 is adapted to receive video data from the video data sources 410. The video display processing system 420 is adapted to generate a composite video image from the received video data. That is, the video display processing system 420 is adapted to combine the received video data into a video image. For example, video data may be received by the video display processing system 420 from four video data sources 410. The video display processing system 420 may then combine the video data into a composite video image by allocating one quarter of the video image to the video data from each of the four video data sources 410. As another example, the video display processing system 420 may generate the composite video image by allocating differently shaped portions of the video image to the video data from each video data source 410, as illustrated in FIG. 3 and FIG. 5. As another example, the video display processing system 420 may combine fewer than all of the received video data into the composite video image. For example, while video data may be received from four video data sources 410, the composite video image may include video data from only two of the video data sources 410.

In certain embodiments, the video display processing system 420 generates the composite video image based at least in part on a configuration. The configuration specifies an arrangement of the video data. That is, the configuration describes how the video display processing system 420 should composite the received video data. For example, the configuration may indicate that video data received from one video data source 410 is to occupy half the screen, while video data from two other video data sources should split the remaining half of the screen one-third and two-thirds, respectively. The configuration may be user defined. That is, a user may specify a preferred arrangement of video data from various video data sources 410. For example, a surgeon might want to display only the following elements from specific systems: from a PACS, historical DR images; from an EMR system, patient allergies, current medications, and family history; from an anesthesiology system, patient vital signs; from a fluoroscopy system, live catheter positioning imagery; and from an ultrasound system, live positioning of needle or tumor.

In certain embodiments, the configuration is based at least in part on a medical procedure. In certain embodiments, the configuration is based at least in part on a medical procedure. For example, for a mammography biopsy procedure, the configuration may indicate that historical PET and ultrasound images be displayed along with live ultrasound and an EMR screen with demographic information and family history for the patient. As another example, for a cardiology procedure such as radio frequency ablation, the configuration may indicate that EKG information and other vital signs from an anesthesiology system be displayed along with live images from a fluoroscopy system and prior images from a PACS such as chest x-rays.

In certain embodiments, the configuration is based at least in part on a hanging protocol. That is, the configuration may be based on and/or include a Default Display Protocol (DDP) similar to that used by other components in a PACS. For example, different clinical scenarios may have different clinical baseline configurations that users may modify.

In certain embodiments, the video display processing system 420 includes a video source input component 421. The video source input component 421 is adapted to receive video data from one or more video data sources 410. For example, the video source input component 421 may handle the reception of streaming video from multiple video data sources 410. As another example, the video display processing system 420 may include multiple video source input components 421. In this configuration, each video source input component 421 may handle a subset of the video data sources 410. This configuration may be desirable when a video source input component 421 is capable of handling a limited number of video data sources 410 and thus multiple video source input components 421 may be used to distribute the processing load of receiving the video data. Alternatively, in the case of multiple video source input components 421, each video source input component 421 may be adapted to receive video data over a different transmission medium. For example, one video source input component 421 may be adapted to receive video data over coaxial cables and another video source input component 421 may be adapted to receive video data as streaming video over a network. As another example, a video source input component 421 may be adapted to receive data over a VGA, DVI, or HDMI input.

In certain embodiments, the video display processing system 420 includes a compositing component 422. The compositing component 422 is adapted to combine video data to generate a composite video image. The video data may be received from the video data sources 410, discussed above, for example. The video data may be the video data received by a video source input component 421, discussed above, for example. The compositing component 422 may generate the composite video image based at least in part on a configuration, similar to the configuration described above.

In certain embodiments, the video display processing system 420 includes a composite video output component 423. The composite video output component 423 is adapted to provide a composite video image. The composite video image may be the composite video image generated by the compositing component 422, discussed above, for example. The composite video image may be provided to a display, such as display 430. The composite video output component 423 may provide the composite video image in a variety of ways. For example, the composite video output component 423 may provide the composite video image over a coaxial video cable. As another example, the composite video output component 423 may provide the composite video image as streaming video over a network.

In certain embodiments, the video display processing system 420 includes a user interface component 424. The user interface component 424 is adapted to receive input from a user. The user may be a healthcare provider such as a physician, for example.

In certain embodiments, the user interface component 424 is adapted to allow a user to change the configuration. For example, a user may change the configuration from a default configuration to a preferred arrangement. As another example, a user may change the configuration to increase the detail provided by a navigation video source for a particular part of a procedure.

In certain embodiments, the user interface component 424 is adapted to allow a user to interact seamlessly with two or more source applications. That is, the user interface component 424 allows a user to interact with applications which generate video data that is provided to the video display processing system 420 as if the user were directly interacting with each application.

In certain embodiments, the user interface component 424 is adapted to provide user input data to a source application. That is, the user interface component 424 provides user input to the source application responsible for providing the video data relevant to the area of the generated composite video image that a user is interacting with.

In certain embodiments, the video display processing system 420 includes an application feedback component 425. The application feedback component 425 is adapted to provide feedback to a source application. The feedback is provided based at least in part on the configuration. For example, the feedback component 425 may notify an application providing video data to the video display processing system 420 that the region of the screen it is being displayed on is only a small portion of the screen. As a result, the source application may provide video data with only a summary or condensed representation of the information the source application includes. If a user later decides to change the configuration, allocating more of the screen to the application, the application feedback component 425 may notify the source application of the change, and in turn, the source application may provide video data with more information. For example, when an anesthesiology application is configured to occupy only narrow portion of the screen, the video data from the application may include only simple graphs and an oxygen-saturation number. When a user later changes the configuration to provide half of the screen to the application, the anesthesiology application may then provide video data with more detailed graphs and a variety of relevant readings.

The display 430 may be a standard display device such as a television, computer monitor, LCD, or plasma screen, for example. The display 430 is adapted to display a video image output from the video display processing system 420. The display 430 may receive the output video image over a coaxial cable or a network, for example. For example, the output video may be provided using streaming video to the display 430.

In certain embodiments, the display 430 includes more than one screen. For example, the display 430 may include two or four screens that act as a single display.

The display 430 may display a composite video image in a manner similar to that illustrated in FIG. 5, discussed below, for example.

The components, elements, and/or functionality of video content distribution system 300 and video content distribution system 400 may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device.

Figure 5:
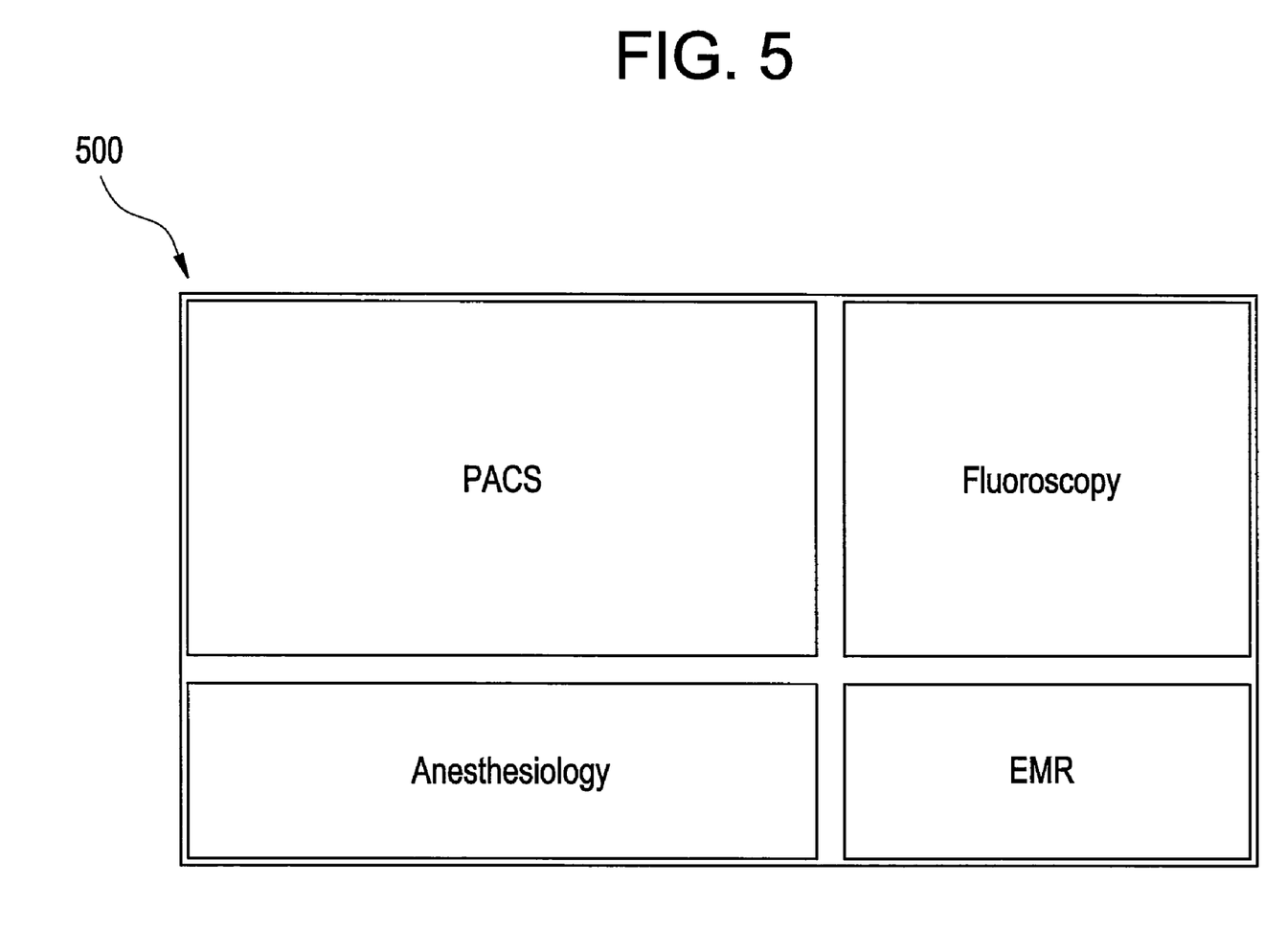
FIG. 5 illustrates an exemplary display screen generated according to an embodiment of the present invention.

FIG. 5 illustrates an exemplary display screen 500 generated according to an embodiment of the present invention. The screen 500 may be displayed on a display similar to the display 330 and/or the display 430, described above, for example.

The display screen 500 shown in FIG. 5 has four video sources configured to be displayed asymmetrically. The screen 500 may be based on a default configuration, for example. For example, the configuration may be the default for a particular type of operation. As another example, the screen 500 may be configured based on a particular user's preference.

The user may seamlessly interact with each of the four applications generating the video data shown in the composited video image. That is, the user may interact with each application's region of the screen 500 as if the user were directly interacting with the application. Such interaction may occur through a user interface component such as the user interface component 424, described above, for example.

Each application generating the video data for each video source may receive feedback about the configuration. For example, the EMR application may receive feedback indicating that its current region of the screen 500 is a small corner, and thus the EMR application may provide only summary information to be displayed. If the user later alters the configuration to give the EMR video data a larger region, the EMR application may provide more information in the video data. The feedback may be provided to the application through an application feedback component similar to the application feedback component 425, described above, for example.

Figure 6:
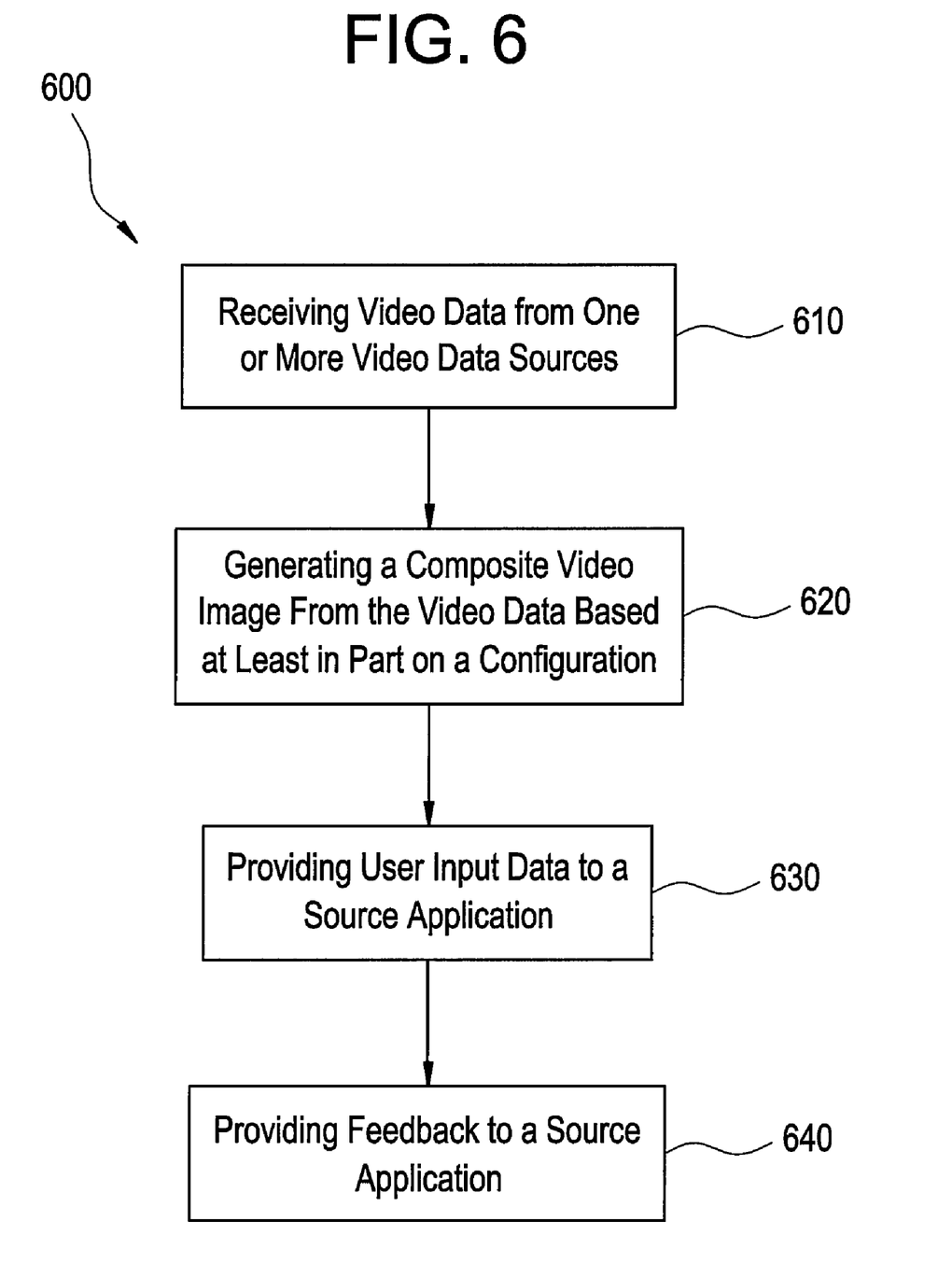
FIG. 6 illustrates a flow diagram for a method for providing composite video according to an embodiment of the present invention.

FIG. 6 illustrates a flow diagram for a method 600 for providing composite video according to an embodiment of the present invention. The method 600 includes the following steps, which will be described below in more detail. At step 610, video data is received from one or more video data sources. At step 620, a composite video image is generated from the video data based at least in part on a configuration. At step 630, user input data is provided to a source application. At step 640, feedback is provided to a source application. The method 600 is described with reference to elements of systems described above, but it should be understood that other implementations are possible.

At step 610, video data is received from one or more video data sources. The video data sources may be similar to the video data sources 310 and/or the video data sources 410, described above, for example. The video data may be received by a video display processing system similar to the video display processing system 320 and/or the video display processing system 420, described above, for example.

The video data may include information intended for display. For example, an application on a video data source may generate video data that is intended to be displayed on a display such as the display. The display may be similar to the display 330 and/or the display 340, described above, for example.

The video data sources may include, for example, a PACS, EMR, anesthesiology, and/or fluoroscopy systems. For example, a video data source may be a PACS workstation. As another example, a video data source may be an imaging modality.

The video data provided by a video data source may be generated at least in part by an application. The application may run at least in part on the video data source. For example, an EMR software application may be running on a computer that is the video data source and provides video data based on the EMR software application. As another example, the video data source may include a software application such as an image view for an imaging modality.

The video data may be communicated over a network, for example. For example, the video data sources may communicate over a wired Ethernet network. As another example, the video data sources may communicate over a wireless network. As another example, the video data sources may communicate over coaxial video cables. The video data may be streaming video communicated to the video display processing system, for example.

In certain embodiments, the video data is received by a video source input component. The video source input component may be similar to the video source input component 421, described above, for example.

At step 620, a composite video image is generated from the video data based at least in part on a configuration. The composite video image may be generated by a video display processing system similar to the video display processing system 320 and/or the video display processing system 420, described above, for example. The video data may be the video data received at step 610, described above, for example.

The composite video image may be generated by combining the received video data. For example, video data may be received from four video data sources. The received video data may then be combined into a composite video image by allocating one quarter of the video image to the video data from each of the four video data sources. As another example, the composite video image may be generated by allocating differently shaped portions of the video image to the video data from each video data source, as illustrated in FIG. 3 and FIG. 5. As another example, the composite video image may include less than all of the received video data. For example, while video data may be received from four video data sources, the composite video image may include video data from only two of the video data sources.

The configuration specifies an arrangement of the video data. That is, the configuration describes how the received video data should be composited. For example, the configuration may indicate that video data received from one video data source is to occupy half the screen, while video data from two other video data sources should split the remaining half of the screen one-third and two-thirds, respectively. The configuration may be user defined. That is, a user may specify a preferred arrangement of video data from various video data sources. For example, a surgeon might want to display only the following elements from specific systems: from a PACS, historical DR images; from an EMR system, patient allergies, current medications, and family history; from an anesthesiology system, patient vital signs; from a fluoroscopy system, live catheter positioning imagery; and from an ultrasound system, live positioning of needle or tumor.

In certain embodiments, the configuration is based at least in part on a medical procedure. In certain embodiments, the configuration is based at least in part on a medical procedure. For example, for a mammography biopsy procedure, the configuration may indicate that historical PET and ultrasound images be displayed along with live ultrasound and an EMR screen with demographic information and family history for the patient. As another example, for a cardiology procedure such as radio frequency ablation, the configuration may indicate that EKG information and other vital signs from an anesthesiology system be displayed along with live images from a fluoroscopy system and prior images from a PACS such as chest x-rays.

In certain embodiments, the configuration is based at least in part on a hanging protocol. That is, the configuration may be based on and/or include a Default Display Protocol (DDP) similar to that used by other components in a PACS. For example, different clinical scenarios may have different clinical baseline configurations that users may modify.

In certain embodiments, the composite video image may be generated by a compositing component. The compositing component may be similar to the compositing component 422, described above, for example.

At step 630, user input data is provided to a source application. The user input data may be received from a user such as a physician or other healthcare provider, for example. In certain embodiments, the user input data is received by a user interface component similar to the user interface component 424, described above, for example.

The user input data is provided to a source application to allow a user to interact seamlessly with two or more source applications. That is, a user may interact with applications which generate video data used to generate the composite video image as if the user were directly interacting with each application.

The user input data is provided to the source application responsible for providing the video data relevant to the area of the generated composite video image that a user is interacting with.

At step 640, feedback is provided to a source application. In certain embodiments, the feedback is provided by an application feedback component similar to the application feedback component 425, described above, for example.

The feedback is provided based at least in part on the configuration. For example, an application providing video data to a video display processing system may be notified that the region of the screen it is being displayed on is only a small portion of the screen. As a result, the source application may provide video data with only a summary or condensed representation of the information the source application includes. If a user later decides to change the configuration, allocating more of the screen to the application, the source application may be notified of the change, and in turn, the source application may provide video data with more information. For example, when an anesthesiology application is configured to occupy only narrow portion of the screen, the video data from the application may include only simple graphs and an oxygen-saturation number. When a user later changes the configuration to provide half of the screen to the application, the anesthesiology application may then provide video data with more detailed graphs and a variety of relevant readings.

One or more of the steps of the method 600 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments of the present invention provide systems and methods for multi-source video distribution and composite display. Certain embodiments provide a technical effect of multi-source video distribution and composite display.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A video display processing system, the system including:
   a video source input component adapted to receive video data from a plurality of video sources, wherein the plurality of video sources includes at least one of a Picture Archiving and Communication System, electronic medical records system, anesthesiology system, and fluoroscopy system;
   a compositing component adapted to generate a composite video image from the video data received from at least two of the plurality of video sources, wherein an arrangement of the video data within the composite video image is based at least in part on a configuration; and
   a composite video output component adapted to output the composite video image.

2. The system of claim 1, further including a user interface component adapted to receive input from a user.

3. The system of claim 2, wherein the user interface component is adapted to allow a user to change the configuration.

4. The system of claim 2, wherein the user interface component is adapted to allow a user to interact seamlessly with the plurality of source applications.

5. The system of claim 2, wherein the user interface component is adapted to provide user input data to a source application, wherein the source application is running at least in part on one of the video sources, wherein the video data from the video source is generated at least in part by the source application.

6. The system of claim 1, further including an application feedback component adapted to provide feedback to a source application, wherein the feedback is provided based at least in part on the configuration.

7. The system of claim 1, wherein at least one source application provides summary video data.

8. The system of claim 1, wherein the configuration is specified based at least in part on a hanging protocol.

9. The system of claim 1, wherein the configuration is based at least in part on a medical procedure.

10. The system of claim 1, wherein the configuration is user defined.

11. A method for providing composite video, the method including:
   performing by at least one processing device, at least:
      receiving video data from a plurality of video sources;
      generating a composite video image from the video data received from at least two of the plurality of video sources, wherein an arrangement of the video data within the composite video image is based at least in part on a configuration; and
      providing feedback to a source application, wherein the feedback is provided based at least in part on the configuration.

12. The method of claim 11, further including providing user input data to a source application, wherein the source application is running at least in part on one of the video sources, wherein the video data from the video source is generated at least in part by the source application.

13. The method of claim 11, wherein at least one source application provides summary video data.

14. The method of claim 11, wherein the configuration is based at least in part on a medical procedure.

15. The method of claim 11, wherein the configuration is user defined.

16. A non-transitory computer-readable medium including a set of instructions for execution on a computer, the set of instructions including:
   a video source input routine configured to receive video data from a plurality of video sources;
   a compositing routine configured to generate a composite video image from the video data received from at least two of the plurality of video sources, wherein an arrangement of the video data within the composite video image is based at least in part on a configuration;
   a composite video output routine configured to output the composite video image; and
   an application feedback routine configured to provide feedback to a source application, wherein the feedback is provided based at least in part on the configuration.

17. The non-transitory computer-readable medium of claim 16, further including a user interface routine configured to provide user input data to a source application, wherein the source application is running at least in part on one of the video sources, wherein the video data from the video source is generated at least in part by the source application.

18. A video display processing system, the system including:
   a video source input component adapted to receive video data from a plurality of video sources;
   a compositing component adapted to generate a composite video image from the video data received from at least two of the plurality of video sources, wherein an arrangement of the video data within the composite video image is based at least in part on a configuration;
   a composite video output component adapted to output the composite video image; and
   an application feedback component adapted to provide feedback to a source application, wherein the feedback is provided based at least in part on the configuration.

19. The system of claim 18, further including a user interface component adapted to receive input from a user.

20. The system of claim 19, wherein the user interface component is adapted to allow a user to change the configuration.

21. The system of claim 19, wherein the user interface component is adapted to allow a user to interact seamlessly with the plurality of source applications.

22. The system of claim 19, wherein the user interface component is adapted to provide user input data to a source application, wherein the source application is running at least in part on one of the video sources, wherein the video data from the video source is generated at least in part by the source application.

23. The system of claim 18, wherein at least one source application provides summary video data.

24. The system of claim 18, wherein the configuration is specified based at least in part on a hanging protocol.

25. The system of claim 18, wherein the configuration is based at least in part on a medical procedure.

26. The system of claim 18, wherein the configuration is user defined.

27. A video display processing system, the system including:
 a video source input component adapted to receive video data from a plurality of video sources;
 a compositing component adapted to generate a composite video image from the video data received from at least two of the plurality of video sources, wherein an arrangement of the video data within the composite video image is based at least in part on a configuration, wherein the configuration is specified based at least in part on a hanging protocol; and
 a composite video output component adapted to output the composite video image.

28. The system of claim 27, further including a user interface component adapted to receive input from a user.

29. The system of claim 28, wherein the user interface component is adapted to allow a user to change the configuration.

30. The system of claim 28, wherein the user interface component is adapted to allow a user to interact seamlessly with the plurality of source applications.

31. The system of claim 28, wherein the user interface component is adapted to provide user input data to a source application, wherein the source application is running at least in part on one of the video sources, wherein the video data from the video source is generated at least in part by the source application.

32. The system of claim 27, wherein at least one source application provides summary video data.

33. The system of claim 27, wherein the configuration is based at least in part on a medical procedure.

34. The system of claim 27, wherein the configuration is user defined.

35. A video display processing system, the system including:
 a video source input component adapted to receive video data from a plurality of video sources;
 a compositing component adapted to generate a composite video image from the video data received from at least two of the plurality of video sources, wherein an arrangement of the video data within the composite video image is based at least in part on a configuration, wherein the configuration is based at least in part on a medical procedure; and
 a composite video output component adapted to output the composite video image.

36. The system of claim 35, further including a user interface component adapted to receive input from a user.

37. The system of claim 36, wherein the user interface component is adapted to allow a user to change the configuration.

38. The system of claim 36, wherein the user interface component is adapted to allow a user to interact seamlessly with the plurality of source applications.

39. The system of claim 36, wherein the user interface component is adapted to provide user input data to a source application, wherein the source application is running at least in part on one of the video sources, wherein the video data from the video source is generated at least in part by the source application.

40. The system of claim 35, wherein at least one source application provides summary video data.

41. The system of claim 35, wherein the configuration is user defined.

42. A method for providing composite video, the method including:
 performing by at least one processing device, at least:
  receiving video data from a plurality of video sources; and
  generating a composite video image from the video data received from at least two of the plurality of video sources, wherein an arrangement of the video data within the composite video image is based at least in part on a configuration, wherein the configuration is based at least in part on a medical procedure.

43. The method of claim 42, further including providing user input data to a source application, wherein the source application is running at least in part on one of the video sources, wherein the video data from the video source is generated at least in part by the source application.

44. The method of claim 42, wherein at least one source application provides summary video data.

45. The method of claim 42, wherein the configuration is user defined.

\* \* \* \* \*